US009125737B2

(12) United States Patent
Artsyukhovich et al.

(10) Patent No.: US 9,125,737 B2
(45) Date of Patent: Sep. 8, 2015

(54) CONSTANT FORCE INTRAOCULAR LENS INJECTOR

(75) Inventors: Alex Artsyukhovich, Dana Point, CA (US); Mikhail Boukhny, Laguna Niguel, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 652 days.

(21) Appl. No.: 12/338,439

(22) Filed: Dec. 18, 2008

(65) Prior Publication Data

US 2010/0160926 A1 Jun. 24, 2010

(51) Int. Cl.
*A61F 9/00* (2006.01)
*A61F 2/16* (2006.01)

(52) U.S. Cl.
CPC .............. *A61F 2/1678* (2013.01); *A61F 2/167* (2013.01); *A61F 2250/0021* (2013.01)

(58) Field of Classification Search
USPC ......................................... 606/107; 623/6.12
See application file for complete search history.

(56) References Cited

U.S. PATENT DOCUMENTS

| 4,681,102 | A | 7/1987 | Bartell |
| 5,275,604 | A | 1/1994 | Rheinish et al. |
| 5,425,734 | A | 6/1995 | Blake |
| 5,494,484 | A | 2/1996 | Feingold |
| 5,499,987 | A | 3/1996 | Feingold |
| 5,616,148 | A | 4/1997 | Eagles et al. |
| 5,620,450 | A | 4/1997 | Eagles et al. |
| 5,653,715 | A | 8/1997 | Reich et al. |
| 5,873,879 | A | 2/1999 | Figueroa et al. |
| 5,928,245 | A | 7/1999 | Wolf et al. |
| 5,944,725 | A | 8/1999 | Cicenas et al. |
| 6,241,737 | B1 | 6/2001 | Feingold |
| 6,312,433 | B1 | 11/2001 | Butts et al. |
| 6,355,046 | B2 | 3/2002 | Kikuchi et al. |
| 6,387,101 | B1 | 5/2002 | Butts et al. |

(Continued)

FOREIGN PATENT DOCUMENTS

| EP | 1360944 A2 | 11/2003 |
| EP | 1958594 | 8/2008 |

(Continued)

OTHER PUBLICATIONS

International Search Report for PCT/US2009/067814, Publication No. WO2010/080351, 5 pages.

(Continued)

*Primary Examiner* — Tuan V Nguyen
(74) *Attorney, Agent, or Firm* — Darien Reddick

(57) ABSTRACT

An intraocular lens injection device comprises a tubular housing with a passageway extending along its longitudinal axis and a plunger shaft disposed within and moveable along the passageway. The tubular housing and the plunger shaft have frictional engaging features that are configured to produce a varying plunging friction as the plunger is moved along its operating range, to offset changes in the plunging resistance that arise from injecting the IOL into the eye. The variable plunging friction may include one or more step changes in unloaded plunging friction, or a curved variation in plunging friction, or both, along at least a portion of the operating range of the plunger shaft. In some embodiments, a slot of varying width in the housing frictionally engages a tab extending transversely from the plunger shaft. In others, a contoured surface on the plunger shaft frictionally engages an orifice in the tubular housing.

26 Claims, 4 Drawing Sheets

(56) References Cited

U.S. PATENT DOCUMENTS

| | | | |
|---|---|---|---|
| 6,398,789 | B1 | 6/2002 | Capetan |
| 6,406,481 | B2 | 6/2002 | Feingold et al. |
| 6,447,519 | B1 | 9/2002 | Brady et al. |
| 6,468,282 | B2 | 10/2002 | Kikuchi et al. |
| 6,471,708 | B2 | 10/2002 | Green |
| 6,491,697 | B1 | 12/2002 | Clark et al. |
| 6,503,275 | B1 | 1/2003 | Cumming |
| 6,506,195 | B2 | 1/2003 | Chambers et al. |
| 7,014,641 | B2 | 3/2006 | Kobayashi et al. |
| 7,156,854 | B2 | 1/2007 | Brown et al. |
| 2002/0151904 | A1 | 10/2002 | Feingold et al. |
| 2005/0149057 | A1* | 7/2005 | Rathert .......... 606/107 |
| 2005/0222578 | A1* | 10/2005 | Vaquero .......... 606/107 |
| 2006/0229634 | A1 | 10/2006 | Shepherd |
| 2008/0200921 | A1* | 8/2008 | Downer .......... 606/107 |
| 2009/0005788 | A1* | 1/2009 | Rathert .......... 606/107 |

FOREIGN PATENT DOCUMENTS

| | | |
|---|---|---|
| EP | 2085053 | 8/2009 |
| JP | 2009-183366 | 8/2009 |
| RU | 2138232 | 9/1999 |
| SU | 1706614 | 1/1992 |
| WO | WO 02/060338 A2 | 8/2002 |
| WO | WO 2007/080868 | 7/2007 |

OTHER PUBLICATIONS

European Search Report and Opinion, EP EP12160448.2, dated Jun. 25, 2012, 5 pages.

PCT International Preliminary Report on Patentability, PCT/US2009/067814, dated Jun. 21, 2011, 6 pages.

* cited by examiner

CONSTANT FORCE INTRAOCULAR LENS INJECTOR

TECHNICAL FIELD

The present invention relates generally to devices for delivering an intraocular lens into an eye and more particularly to techniques for compensating for variations in resistance to injection of the lens.

BACKGROUND

The human eye functions to provide vision by transmitting light through a clear outer portion called the cornea, and focusing the image by way of a crystalline lens onto a retina. The quality of the focused image depends on many factors, including the size and shape of the eye and the transparency of the cornea and lens. When age or disease causes the lens to become less transparent, vision deteriorates because of the diminished light transmitted to the retina. This deficiency in the lens of the eye is known as a cataract, and may be treated by surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

The IOL is injected into the eye through the same small incision used to remove the diseased lens. An insertion cartridge of an IOL injector is loaded with the IOL, the tip of the insertion cartridge is inserted into the incision, and the lens is delivered into the eye.

Many IOLs manufactured today are made from a polymer with specific characteristics. These characteristics allow the lens to be folded, and when delivered into the eye, allow the lens to unfold into the proper shape. Several manual injector devices are available for implanting these lenses into the eye. However, threaded-type manual injectors require the use of two hands, which is cumbersome and tedious. Syringe-type injectors produce inconsistent injection force and displacement. Thus, improved devices and methods are needed for delivering IOLs into the eye.

SUMMARY

Embodiments of the present invention include a device for injecting an intraocular lens into an eye, the device including a tubular housing with a passageway extending along its longitudinal axis and a plunger shaft disposed within and moveable along the passageway. The tubular housing and the plunger shaft have frictional engaging features that are configured to produce a varying plunging friction as the plunger is moved along its operating range, to offset one or more changes in the plunging resistance that arise from injecting the IOL into the eye. In some cases, the frictional engaging features are designed to produce a plunging friction that varies according to a pre-determined unloaded friction profile designed to complement, or at least partially offset, corresponding changes in the plunging resistance characteristic to injection of the IOL. These changes may include, for example, changes in plunging resistance characteristic to folding of the intraocular lens, or changes in plunging resistance associated with the insertion of the folded intraocular lens into the anterior chamber eye, or both. The variable plunging friction may comprise one or more step changes in unloaded plunging friction, or a curved variation in plunging friction, or both, along at least a portion of the operating range of the plunger shaft.

In some embodiments of the invention, the frictional engaging features may comprise a slot extending longitudinally along the tubular housing and a tab extending transversely from the plunger shaft and frictionally engaging with the side walls of the slot as the plunger shaft is translated back and forth. In these embodiments, variable plunging friction is induced by a variation in the slot's width. In other embodiments, the frictional engaging features comprise an orifice that is integral to or rigidly disposed within the tubular housing, so that a contoured plunger shaft frictionally engages the orifice as the plunger shaft is moved back and forth. In some of these embodiments the contours of the plunger shaft may comprise one or more step changes to a thickness of the plunger shaft, a curved variation in thickness of the plunger shaft, or one or more changes in the plunger shaft's surface texture, along at least a portion of the length of the plunger shaft.

In some embodiments the variation in plunging friction may be designed to closely complement the expected plunging resistance, so that the net plunging resistance in operation is more or less constant. In other embodiments, the resolution of plunging friction variation may be less fine, so as to only offset major shifts in injection resistance force.

Of course, those skilled in the art will appreciate that the present invention is not limited to the above features, advantages, contexts or examples, and will recognize additional features and advantages upon reading the following detailed description and upon viewing the accompanying drawings.

DETAILED DESCRIPTION

Reference is now made in detail to the exemplary embodiments of the invention, examples of which are illustrated in the accompanying drawings.

Figure 1:
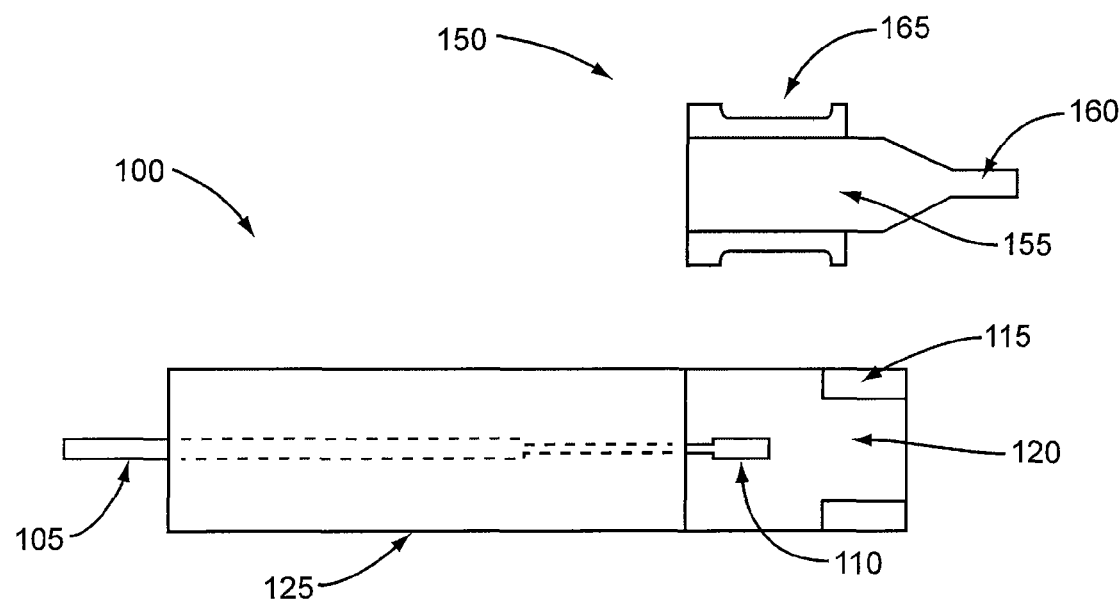
FIG. 1 is a top view of a cartridge and hand piece that collectively function as an intraocular lens injector.

FIG. 1 is a top cross-sectional view of a cartridge and hand piece that collectively function as an intraocular lens (IOL) injector. In the embodiment pictured in FIG. 1, a two-piece IOL injector system includes hand piece 100 and cartridge 150. Hand piece 100 comprises a tubular injector housing 125, which houses a plunger shaft 105 connected to a plunger 110. Plunger shaft 105 is typically rigid and is connected to plunger 110 such that movement of shaft 105 translates into movement of plunger 110. In this manner, plunger 110 is designed to translate longitudinally along and within injector housing 125. Those skilled in the art will appreciate that plunger shaft 105 and plunger 110 may comprise a unitary piece, e.g. of molded plastic, in some embodiments, or may comprise two or more parts that are assembled together, e.g., by way of a snap fit, a threaded fitting, or the like. In some embodiments, plunger 110 may comprise or may be part of a removable plunger tip, which may be disposable.

In the pictured embodiment, two tabs 115 are located on one end of hand piece 100 and area 120 is adapted to receive cartridge 150. Cartridge 150, which may be a disposable unit designed for one-time use, includes two tabs 165, a nozzle 160, and a chamber 155. Chamber 155 holds an IOL. Nozzle 160 is hollow and is designed to allow the IOL to pass through it and into an eye. The interior of cartridge 150 contains a continuous passage that includes chamber 155 and nozzle 160. Thus, an IOL positioned in chamber 155 can be transferred out of cartridge through nozzle 160.

Figure 2:
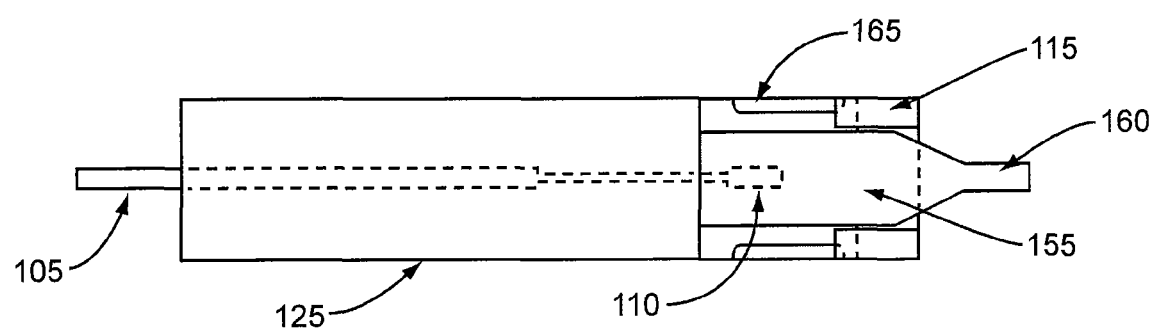
FIG. 2 is another top view of a cartridge and hand piece that collectively function as an intraocular lens injector.

FIG. 2 illustrates how cartridge 150 and hand piece 100 fit together. As depicted in the embodiment shown in FIG. 2, cartridge 150 is located in area 120. Plunger 110 is designed to translate within the tubular injector housing 125 and into and through chamber 155. Plunger shaft 105 and plunger 110 are thus generally constrained to move longitudinally within housing 125 and the attached cartridge 150. The tabs 165 on cartridge 150 are designed to fit under the tabs 115 on hand piece 100. Positioned thus, cartridge 150 is secured to hand piece 100.

In operation, plunger shaft 105 is moved, i.e., translated longitudinally, causing plunger 110 to move correspondingly. To insert cartridge 150, plunger shaft 105 and plunger 110 are drawn back so that plunger 110 is located outside of area 120. Area 120 receives cartridge 150, and plunger 110 is advanced into cartridge 150. In particular, plunger 110 is designed to enter chamber 155 and contact the IOL contained in chamber 155. When plunger 110 is advanced further, the IOL is folded, compressed, and pushed out of chamber 155 through nozzle 160. Before operation of the IOL injector, nozzle 160 is inserted into an incision made in the cornea or conjuctiva, thus allowing the IOL to be delivered into the eye.

Figure 3:
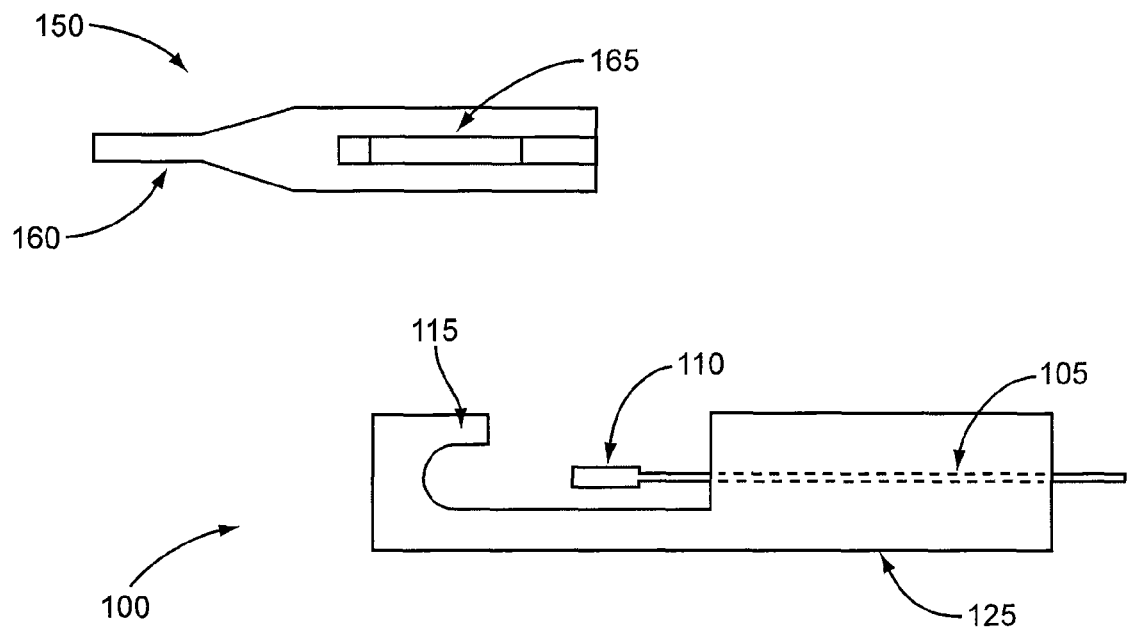
FIG. 3 is a side view of a cartridge and hand piece that collectively function as an intraocular lens injector.
Figure 4:
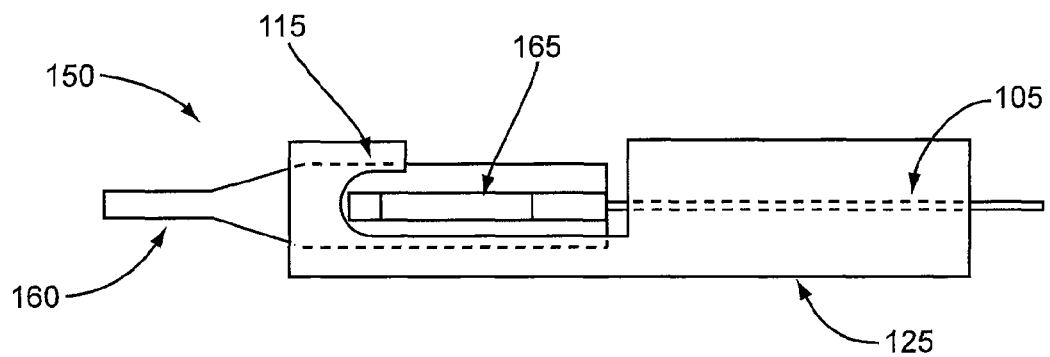
FIG. 4 is another side view of a cartridge and hand piece that collectively function as an intraocular lens injector.

FIGS. 3 and 4 show a side cross-sectional view of the cartridge 150 and hand piece 100 depicted in FIGS. 1 and 2. In this embodiment, cartridge 150 fits into hand piece 100 as shown. In FIG. 4, plunger shaft 105 has been translated out of the way, so that cartridge 150 can be installed onto the injector body 125, and then translated forward so that plunger 110 is inside chamber 155 of cartridge 150.

In the IOL injector embodiments pictured in FIGS. 1-4, the cartridge 150 is designed so that the lens is folded into a tight package for insertion into the eye through a small incision. In particular, translation of the plunger shaft 105 causes the plunger 110 to push the lens through a narrowing channel within cartridge 150, which is filled with viscoelastic lubricant. As the diameter of the channel decreases, the IOL is folded and compressed in a package with a small cross section, to fit through an incision that may be as small as 2-3 millimeters.

As the IOL is pushed through the cartridge, resistance to the plunging motion is induced by the interaction among the plunger 110, the IOL, the viscoelastic fluid, the internal contours of the cartridge 150, and the eye itself. This resistance, which can be understood as the load applied to the plunger by the IOL as it passes through the cartridge and into the eye, varies as the plunger is translated into and through the cartridge 150.

Figure 5A:
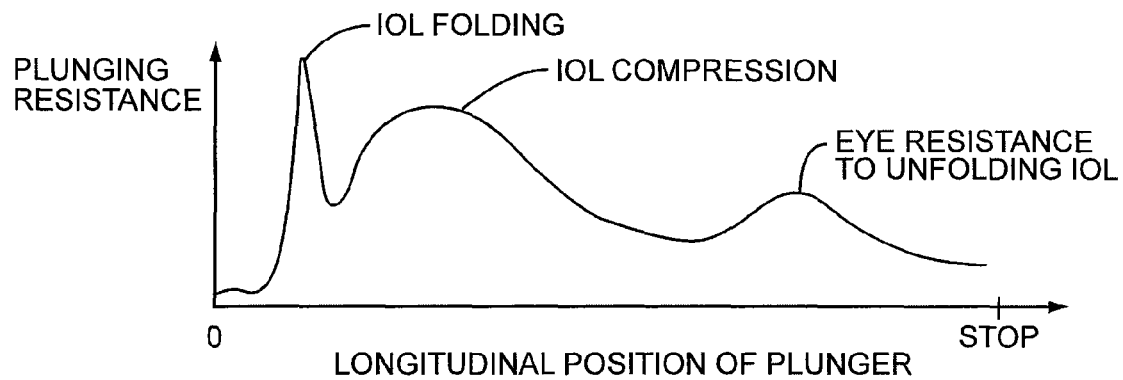
FIGS. 5A, 5B, and 5C illustrate a characteristic plunging resistance profile, an unloaded plunging friction profile according to some embodiments of the present invention, and a profile of total resistance to IOL injection, respectively.

FIG. 5A schematically graphs an example of variation in plunging resistance as the plunger 100 is translated from a starting longitudinal position (designated as "0" in FIG. 5A) to a stopping position ("STOP") corresponding to the point at which the IOL is fully inserted into the eye. As seen in FIG. 5A, the resistance to plunger motion increases dramatically as the plunger engages the IOL and as the IOL is folded within the cartridge 150. Following a drop in force after the IOL is folded, the plunging resistance increases again as the IOL is compressed by being pushed through a channel with decreasing diameter. When the IOL begins to exit the tip of the injector, the resistance to plunger drops. In some cases, this drop in resistance can be quite rapid, so that the lens tends to "shoot" out of the cartridge 150. A small peak in resistance follows, as fluid in the eye pushes back against the unfolding IOL.

These variations in plunging resistance are undesirable, since they can make injection of the IOL a difficult procedure. For instance, a rapid drop in plunging resistance as the IOL exits the cartridge 150 can result in the IOL overshooting an ideal central position in the lens capsule, which might require the surgeon to re-enter the eye and correct the position. In general, variations in resistance to injection of IOL require the surgeon to vary force applied to IOL injector plunger in order to smoothly inject the IOL. To avoid overshoot, the surgeon must quickly react to decreases in plunging resistance, and decrease the pushing force applied to the plunger shaft 105.

Various embodiments of the present invention reduce or eliminate this variation in resistance force, making IOL injection more even, predictable, and well controlled through one or more of the above-described phases of the IOL injection process. In general, this may be done by designing the injector so that its plunger shaft and body interact to produce an unloaded plunging friction that varies in a complementary manner to the expected plunging resistance in operation.

Figure 5B:
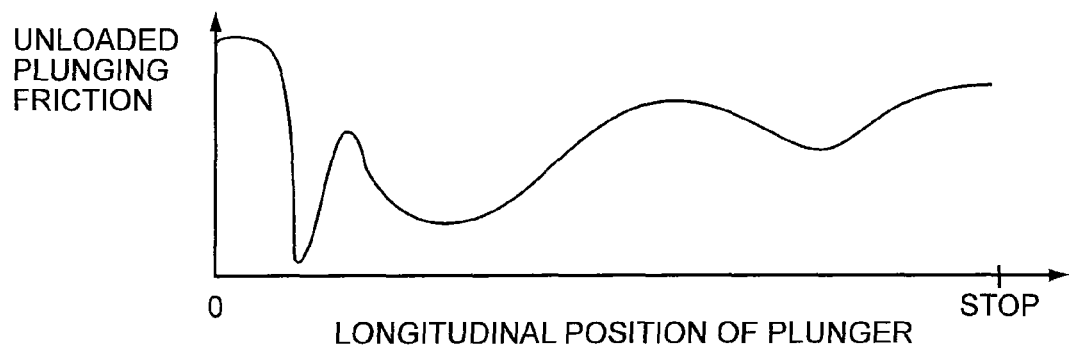
Figure 5C:
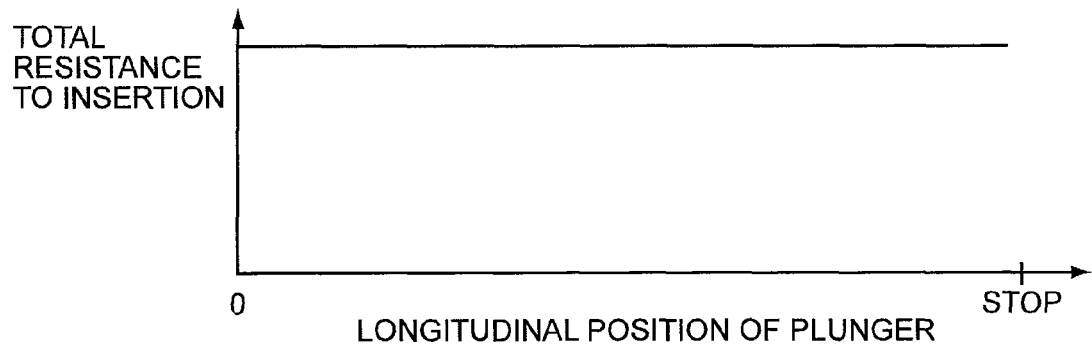

This is illustrated in the idealized unloaded plunging friction profile of FIG. 5B, which illustrates an unloaded plunging friction that varies from the plunger's starting position (at "0") to its stopping position (at "STOP"). This unloaded plunging friction can be understood to represent the resistance to longitudinal translation of the plunger in an unloaded state, i.e., without an IOL, viscoelastic fluid, etc. As pictured, the unloaded plunging friction of FIG. 5B mirrors exactly the characteristic plunging resistance of the IOL folding and insertion operation pictured in 5A. Accordingly, as shown in FIG. 5C, the sum of the plunging resistance of FIG. 5A and the unloaded plunging resistance profile of FIG. 5B is the constant-resistance profile of FIG. 5C.

The variation in resistance to injection as an operator pushes on the IOL plunger shaft can be reduced by introducing, by design, a variable friction force that also varies with plunger position. In general, these designed variations in friction force along the operating range of the plunger should offset, at least partially, one or more of the changes in plunging resistance that characteristically arise from injection of the lens into the eye. In this manner, the total resistance to injection will be closer to constant, making IOL injection smoother and more predictable.

Figure 6:
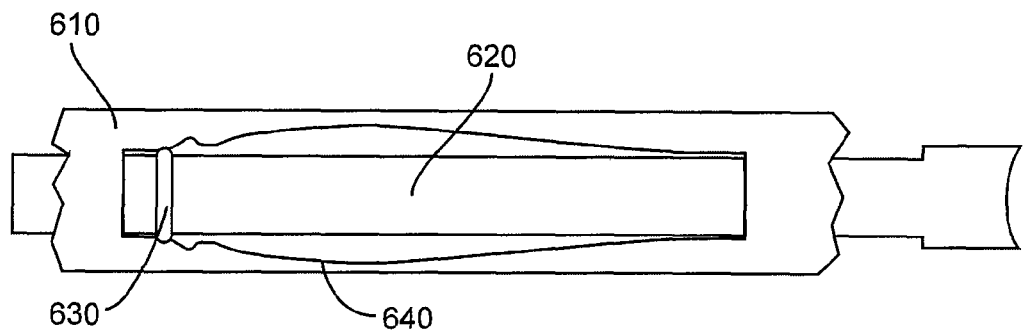
FIG. 6 illustrates details of an IOL injector body and plunger shaft according to some embodiments of the invention.

There are various ways to create variable friction force as a plunger shaft is translated along a tubular body of an intraocular lens injector device. One technique is pictured in FIG. 6, which illustrates a plunger shaft 620 passing through a passageway along a portion of a tubular body 610. In this embodiment, a tab 630 extends from the plunger shaft 620 through a slot 640 in the body 610, so that the tab 630 slides along the slot 640 as the plunger shaft 620 is translated back and forth. The variation in friction in this embodiment is introduced by the varying width of slot 640, which engages the tab 630 with varying frictional force as the slot width increases and decreases. Although the slot's width variation in FIG. 6 is greatly exaggerated, for the sake of visibility, those skilled in the art will appreciate that an appropriately dimensioned slot 640 will engage the tab 630 with a frictional force that varies with its width. Those skilled in the art will further appreciate, of course, that the exact frictional force at any given point will depend not only on the width of the slot 640 but also on the thickness of the tab 630 and the relative compliance of the materials from which the tab 630 and the body 610 are composed, as well as the surface finishes on those components. Furthermore, the resistance force at any given point will also vary with the speed of the plunger movement. Generally speaking, however, the tab 630 and the slot 640 can be designed to engage so as to produce an unloaded resistance that varies in a desired manner over a reasonable range of plunger speeds.

For instance, FIG. 6 illustrates a smoothly varying width of slot 640. If carefully designed, the unloaded plunging resistance produced by the engagement between the tab 630 and the slot 640 can be generally complementary to the expected plunging resistance arising from folding the lens and inserting it into the eye. In some cases, the sum of the varying plunging friction and the plunging resistance may thus be substantially flat over at least a pre-determined portion of the operating range of the plunger shaft. Those skilled in the art will appreciate, however, that a variety of profiles for the variation in slot width may be used. For instance, the variation in slot width may comprise one or more step changes in width, rather than the curved profile illustrated in FIG. 6. Furthermore, although the slot 640 in FIG. 6 is curved along both side walls, other embodiments may include a slot that has only a single curved or stepped side wall, with the other side wall being straight. Still other embodiments may comprise a mixture of curved, stepped, or straight side walls, to introduce frictional resistance variations at differing resolution along the operating range of the plunger.

Figure 7:
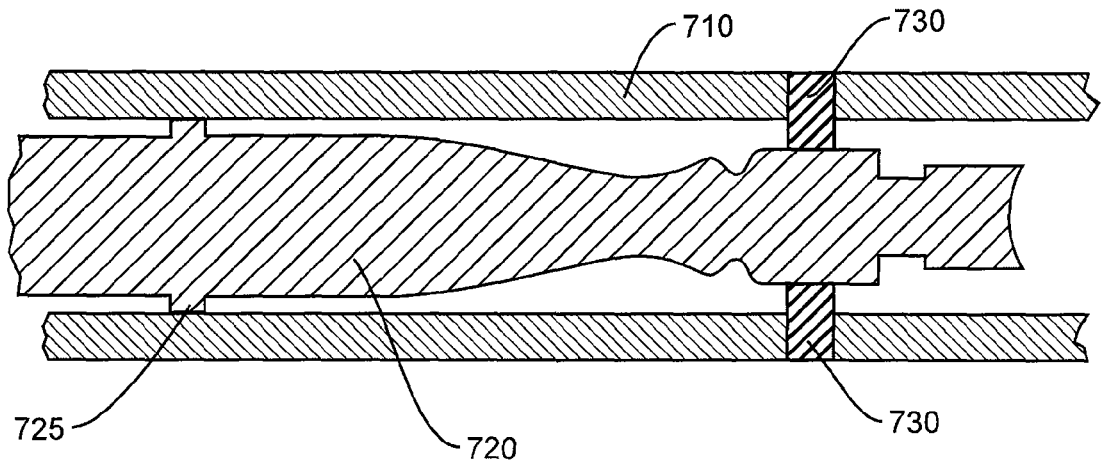
FIG. 7 illustrates details of an IOL injector body and plunger shaft according to further embodiments of the invention.

FIG. 7 illustrates a cut-away view of another embodiment of the present invention, in which a variably dimensioned plunger shaft 720 passes along a passageway in tubular body 710. At one end, plunger shaft 720 passes through an orifice 730, which frictionally engages the plunger shaft 720. The contoured plunger shaft 720 is compressed by the orifice 730 to varying degrees as it is translated through the orifice 730, causing a predictable variation in plunging friction as the plunger moves from a starting position to a stopping position defined by the stop tabs 725. In some embodiments, the orifice 730 may be integral to a tubular housing, e.g., molded as a single piece of plastic, while in other embodiments the orifice 730 may instead comprise one or more components, such as a washer, that are rigidly connected to or securely held within the tubular housing 710.

Similarly to the embodiment of FIG. 6, the embodiment of FIG. 7 will produce a precise frictional force at any given point in the movement of the plunger shaft 720 that depends not only upon the dimensions of plunger shaft 720 and orifice 730, but also upon the relative compliance of the orifice 730 and the plunger shaft 720, as well as upon the surface finishes of the materials. In some embodiments, the plunger shaft 720 might be composed of a relatively compliant material, such as Teflon, compared to a relatively non-compliant orifice 730, which might be formed from metal, for instance, or from hard plastic. Of course, those skilled in the art will appreciate that the reverse approach might be applied to some embodiments, so that a relatively hard plunger shaft 720 passes through a relatively soft orifice 730. Either or both of the plunger shaft 720 and the orifice 730 may be replaceable, in some embodiments, to minimize concerns with wear.

Those skilled in the art will appreciate once more that the contours of plunger shaft 720 are greatly exaggerated in FIG. 7. Those skilled in the art will further appreciate that the details of the contours may vary considerably from the illustrated curved contours. For instance, the contours may comprise one or more step changes in plunger shaft thickness, or a combination of curves and one or more step changes. Further, although the plunger shaft 720 might have a circular cross section, in some embodiments, with a radius that varies along the length of the plunger shaft 720, other embodiments might have a different cross-sectional shape. Thus, for example, a plunger shaft with a generally rectangular cross section might have a curved and/or stepped contour on only one or two sides. As another example, a plunger shaft might have a generally round cross section, but with one flat surface, so that the shaft is "keyed" to the orifice and not permitted to rotate.

Figure 8:
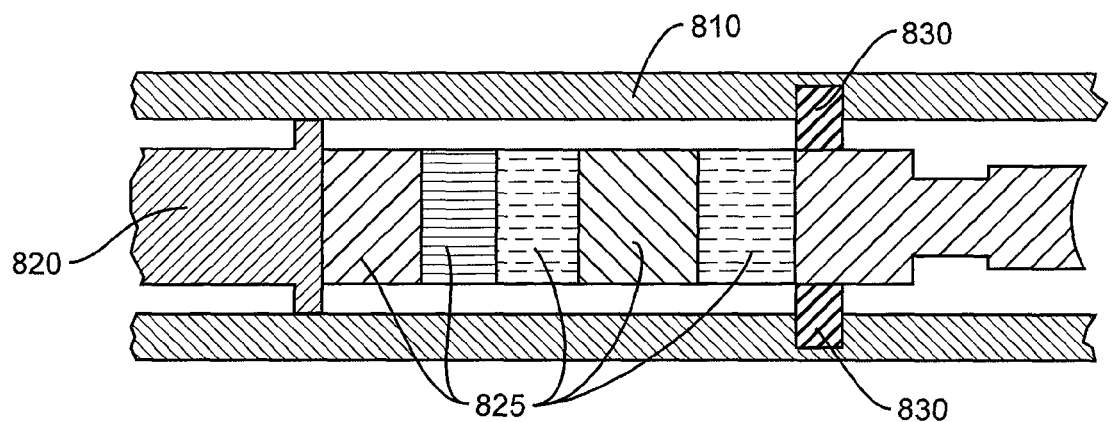
FIG. 8 illustrates details of an IOL injector body and plunger shaft according to still further embodiments of the invention.

Yet another possible embodiment of the present invention is shown in FIG. 8. Here, the plunger shaft 820 has generally constant dimensions over most of its length, but has surface contours, or texture, that varies along the length. In operation, the plunger shaft passes through an orifice 830, which is rigidly fastened to tubular body 810. In this case, however, a variation in frictional force is induced by the engagement of the orifice 830 with varying surface textures 825 on the plunger shaft 820. As illustrated in FIG. 8, these textures may be disposed in a series of distinct regions, thus inducing a series of step changes in plunging friction. Of course, more gradual changes in plunging friction may be introduced by using smaller regions of varying texture, or by introducing more continuous changes in texture. The varying texture may be introduced by a variety of means, including, but not limited to, by adding knurling to the plunger's surface, e.g., with knurls of varying dimension and/or at variable spacing.

The preceding descriptions of various embodiments of an intraocular lens injection device, as well as the accompanying figures, have been provided for purposes of illustration and example. In view of this description and these figures will appreciate that the various embodiments of the present invention are generally directed to a device for injecting an intraocular lens into an eye, the device including a tubular housing with a passageway extending along its longitudinal axis and a plunger shaft disposed within and moveable along the passageway over an operating range. As exemplified by the embodiments of FIGS. 6, 7, and 8, the tubular housing and the plunger shaft have frictional engaging features that are configured to produce a varying plunging friction as the plunger is moved along its operating range, to offset one or more changes in the plunging resistance that arise as the IOL is injected into the eye. In some cases, the frictional engaging features are designed to produce a plunging friction that varies according to a pre-determined unloaded friction profile designed to complement, or at least partially offset, corresponding changes in the plunging resistance characteristic to injection of the IOL. As shown above, the variable plunging friction may comprise one or more step changes in unloaded plunging friction, or a curved variation in plunging friction, or both, along at least a portion of the operating range of the plunger shaft.

In some embodiments of the invention, the frictional engaging features may comprise a slot extending longitudinally along the tubular housing and a tab that extends transversely from the plunger shaft and frictionally engages with the side walls of the slot as the plunger shaft is translated back and forth. Variable plunging friction may be induced by a variation in the slot's width.

In other embodiments, the frictional engaging features may comprise an orifice that is integral to or rigidly disposed within the tubular housing, so that a contoured plunger shaft frictionally engages the orifice as the plunger shaft is moved back and forth. In some embodiments the contours of the plunger shaft may comprise one or more step changes to a thickness of the plunger shaft, a curved variation in thickness of the plunger shaft, or one or more changes in the plunger shaft's surface texture, along at least a portion of the length of the plunger shaft.

As discussed above, in some embodiments the variation in plunging friction may be designed to closely complement the expected plunging resistance, so that the net plunging resistance in operation is more or less constant. In other embodiments, the resolution of plunging friction variation may be less fine, so as to only offset major shifts in injection resistance force. In some embodiments, for example, only a single region of elevated friction force may be used to offset a swift drop in plunging resistance near the end of the injection operation, to prevent overshooting of the IOL. In any of these embodiments, variation in plunging resistance is reduced or eliminated, resulting in reduced problems with lens overshoot and more consistent and well controlled IOL injection, thus requiring less dexterity and concentration from the surgeon.

Those skilled in the art will appreciate, of course, that the present invention may be carried out in other ways than those specifically set forth herein without departing from essential characteristics of the invention. The present embodiments are thus to be considered in all respects as illustrative and not restrictive, and all changes coming within the meaning and equivalency range of the appended claims are intended to be embraced therein.

What is claimed is:

1. A device for injecting an intraocular lens into an eye, the device comprising:
    a tubular housing having a longitudinal axis and a passageway along the longitudinal axis;
    an orifice formed and fixed within the passageway of the tubular housing, the orifice having an opening, a cross-sectional size of the opening of the orifice being different than a cross-sectional size of the passageway, the cross-section of the orifice and the cross-section of the passageway being transverse to the longitudinal axis; and
    a plunger shaft disposed within and moveable along the passageway of the body over an operating range, the plunger shaft comprising a contoured surface that includes a contour that varies in a direction along a longitudinal axis of the plunger shaft, the contoured surface operable to engage the orifice to vary plunging friction along the operating range to offset one or more changes in plunging resistance arising from injection of the lens into the eye.

2. The device of claim 1, wherein the orifice and the contoured surface operably engage each other to produce the varying plunging friction according to a pre-determined unloaded plunging friction profile having one or more changes in plunging friction that complement corresponding changes in plunging resistance characteristic to injection of the lens into the eye.

3. The device of claim 2, wherein the orifice and the contoured surface operably engage each other to produce one or more changes in plunging friction to complement changes in plunging resistance characteristic to folding of the intraocular lens, or to complement changes in plunging resistance characteristic to insertion of the intraocular lens into the eye, or both.

4. The device of claim 2, wherein the pre-determined unloaded plunging friction profile comprises one or more step changes in unloaded plunging friction along the operating range of the plunger shaft.

5. The device of claim 2, wherein the pre-determined unloaded plunging friction profile comprises a curved variation in plunging friction over at least a portion of the operating range of the plunger shaft.

6. The device of claim 2, wherein the orifice and the contoured surface operably engage each other so that the sum of the varying plunging friction and the plunging resistance characteristic to injection of the lens into the eye is substantially flat over a pre-determined portion of the operating range of the plunger shaft.

7. The device of claim 1, wherein the orifice is integral to or rigidly connected to the tubular housing.

8. The device of claim 7, wherein the contoured surface comprises one or more step changes to a thickness of the plunger shaft.

9. The device of claim 7, wherein the contoured surface comprises a curved change in a thickness of the plunger shaft along at least a portion of the length of the plunger shaft.

10. The device of claim 1, wherein the orifice has an opening smaller than an opening of the passageway.

11. The device of claim 1, wherein the contoured surface is a continuously contoured surface over at least a portion of a length of the plunger shaft.

12. The device of claim 1, wherein the plunger shaft comprises varying radii along a length thereof defining the contoured surface.

13. The device of claim 1, wherein a diametrical cross-section of the plunger shaft varies along a length thereof defining the contoured surface.

14. The device of claim 1, wherein the contoured surface comprises at least one step change in plunger shaft thickness.

15. The device of claim 1, wherein a thickness of the plunger shaft varies along a length thereof to define the contoured surface.

16. The device of claim 1, wherein the plunger shaft comprises a non-circular cross-sectional shape along at least a length of the plunger shaft.

17. The device of claim 1, wherein the plunger shaft further comprises a stop tab at a location along a length thereof, the stop tab adapted to contact an end wall defining the orifice to define a stopping position of the plunger shaft.

18. A device for injecting an intraocular lens into an eye, the device comprising:
    a tubular housing having a longitudinal axis and a passageway along the longitudinal axis; and
    a plunger shaft disposed within and moveable along the passageway of the body over an operating range;
    the tubular housing and the plunger shaft having frictional engaging features that engage each other, the frictional engaging features defining a variable plunging friction force along the operating range between the tubular housing and the plunger shaft to offset one or more changes in plunging resistance arising from injection of the lens into the eye, wherein the frictional engaging features comprise:

an orifice disposed within the passageway and defining a cross-sectional opening smaller than a cross-sectional size of the passageway, the cross-section of the orifice and the cross-section of the passage being transverse to the longitudinal axis, wherein the orifice is disposed at a fixed position within the passageway; and wherein the frictional engaging features comprise:

a contoured surface on the plunger shaft that includes a contour that varies in a direction along a longitudinal axis of the plunger shaft, the contoured surface frictionally engaging the orifice as the plunger shaft is translated along the operating range.

19. The device of claim 18, wherein the variable plunging friction force varies according to a pre-determined unloaded plunging friction profile having one or more changes in plunging friction that complement corresponding changes in plunging resistance.

20. The device of claim 19, wherein the variable plunging friction force is variable to complement changes in plunging resistance characteristic to folding of the intraocular lens, or to complement changes in plunging resistance characteristic to insertion of the intraocular lens into the eye, or both.

21. The device of claim 19, wherein the pre-determined unloaded plunging friction profile comprises one or more step changes in unloaded plunging friction along the operating range of the plunger shaft.

22. The device of claim 19, wherein the pre-determined unloaded plunging friction profile comprises a curved variation in plunging friction over at least a portion of the operating range of the plunger shaft.

23. The device of claim 18, wherein the sum of the variable plunging friction force and the plunging resistance is substantially flat over a pre-determined portion of the operating range of the plunger shaft.

24. The device of claim 18, wherein the contoured surface on the plunger shaft frictionally engages the orifice as the plunger shaft is translated along the operating range.

25. The device of claim 18, wherein the contoured surface comprises one or more step changes to a thickness of the plunger shaft.

26. The device of claim 18, wherein the contoured surface comprises a curved change in a thickness of the plunger shaft along at least a portion of the length of the plunger shaft.

* * * * *